United States Patent
Shukla et al.

(10) Patent No.: US 7,999,112 B2
(45) Date of Patent: Aug. 16, 2011

(54) REUSABLE TRANSITION METAL COMPLEX CATALYST USEFUL FOR THE PREPARATION OF HIGH PURE QUALITY 3,3'-DIAMINOBENZIDINE AND ITS ANALOGUES AND A PROCESS THEREOF

(75) Inventors: Ravi Kant Shukla, Maharashtra (IN); Lourduswamy Emmanuvel, Maharashtra (IN); Chidambaram Rameshkumar, Maharashtra (IN); Suryavanshi Gurunath, Maharashtra (IN); Arumugam Sudalai, Maharashtra (IN); Swati Shantikumar Kulkarni, Maharashtra (IN); Swaminathan Sivaram, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 565 days.

(21) Appl. No.: 12/075,585

(22) Filed: Mar. 11, 2008

(65) Prior Publication Data
US 2009/0131678 A1 May 21, 2009

(30) Foreign Application Priority Data
Nov. 13, 2007 (IN) ............................ 2368/DEL/2007

(51) Int. Cl.
*C07F 15/00* (2006.01)

(52) U.S. Cl. ........................................ 548/108; 556/137
(58) Field of Classification Search .................. 548/108; 556/137
See application file for complete search history.

(56) References Cited

OTHER PUBLICATIONS

Ramesh Kumar et al. "Sulfonamide- and hydrazine-based palladium catalysts: Stable and efficient catalysts for C—C coupling reactions in aqueous medium" Journal of Molecular Catalysis A: Chemical 2007, vol. 269, pp. 218-224.*

* cited by examiner

*Primary Examiner* — Joseph Kosack
(74) *Attorney, Agent, or Firm* — Ladas & Parry LLP

(57) ABSTRACT

The present invention provides a reusable transition metal complex catalyst useful for the preparation of high pure quality 3,3'-diaminobenzidine and its analogues. The present invention also provides to a process for the preparation of a reusable transition metal complex catalyst. The present invention further provides a process for the preparation of 3,3'-diaminobenzidine (DAB) or 3,3',4,4' Tetraminobiphenyl (TAB) using reusable transition metal complex catalyst. The high quality 3,3'-diaminobenzedine (DAB) and its analogues are prepared by coupling 4-halo-2-nitroaniline to 3,3'-dinitrobenzidine (DNB) using transition metals as catalysts followed by reduction of 3,3'-dinitrobenzidine to the corresponding substituted 3,3'-diaminobenzidine of formula 1 in high yields.

7 Claims, No Drawings

REUSABLE TRANSITION METAL COMPLEX CATALYST USEFUL FOR THE PREPARATION OF HIGH PURE QUALITY 3,3'-DIAMINOBENZIDINE AND ITS ANALOGUES AND A PROCESS THEREOF

FIELD OF THE INVENTION

The present invention relates to a reusable transition metal complex catalyst useful for the preparation of high pure quality 3,3'-diaminobenzidine and its analogues. The present invention also relates to a process for the preparation of a reusable transition metal complex catalyst. The present invention also relates to a process for the preparation of 3,3'-diaminobenzidine (DAB) or 3,3',4,4' Tetraminobiphenyl (TAB) using reusable transition metal complex catalyst. More particularly, the present invention relates to a process for the preparation of pure high quality 3,3'-diaminobenzedine (DAB) and their analogues by coupling 4-halo-2-nitroaniline to 3,3'-dinitrobenzidine (DNB) using transition metals as catalysts followed by reduction of 3,3'-dinitrobenzidine to the corresponding substituted 3,3'-diaminobenzidine of formula 1 in high yields.

Formula-1:

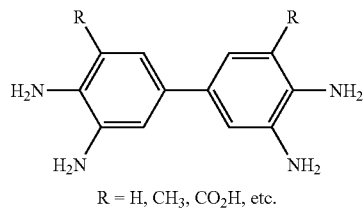

R = H, CH$_3$, CO$_2$H, etc.

BACKGROUND OF THE INVENTION 3,3',4,4'-Tetraaminobiphenyl (TAB) is a valuable intermediate and final product in various areas. For example, TAB is used as monomer in the preparation of polybenzimidazole (PBI) polymers, which are characterized by excellent thermal and mechanical stability. The PBI polymers are widely used as proton-conducting materials for fuel cell applications (compare U.S. Pat. Nos. 2,895,948, 3,174,947, 5,317,078 and 6,187,231). TAB is also used as an antioxidant and as an agent for stabilizing epoxide resins.

In the prior art, TAB was prepared by four known methods. One such known method is ammonolysis of 3,3'-dichlorobenzidine (DAB) in the presence of mainly Cu catalysts (both copper salts and elemental Cu) using aqueous NH$_3$. For example, French Patent Specification No 1,475,631 describes such an ammonolysis of DCB, in the presence of a Cu—I salt and/or of Cu$_2$O and CaCl$_2$ at an elevated temperature preferably 150-210° C. and under an elevated inert gas pressure. The crude TAB thus obtained is purified via its salt formation with a strong acid (yield of TAB is about 70% of theory). Subsequently, various attempts were made to obtain TAB in highly pure form and in high yields from crude TAB as shown below.

The process of U.S. Pat. No. 3,865,876 describes the improvement on the result of the method in accordance with the above mentioned French Patent Specifications by using essentially only CuCl as a catalyst in the ammonolysis of DCB. The yield of TAB of theory having purity of about 75-82% is between about 85 and 87%. This product has a Cu content of about 3-6% by weight. The process of U.S. Pat. No. 3,943,175 (CuCl/Cu powder can also be used as catalyst, in addition to CuCl) describes the purification of TAB (converting it into its sulfate by means of sulfuric acid, isolation of the sulfate and liberation there from of TAB by means of a base). The TAB thus liberated is dissolved and reprecipitated from an aqueous solution advantageously with the addition of activated charcoal and diatomaceous earth. However, the Cu content present in TAB is about 0.6 to 0.9% and the yield at most 45.7% of theory, relative to DCB employed. The German Patent (Ger. Offen. DE 3,111,470) discloses the purification of crude TAB (obtained by ammonolysis process) by boiling it with H$_2$O containing activated carbon and sodium dithionate (yield of TAB is 75.9% with ≦0.0005% Cu content). The Japanese Patent (JP 60,158,146) also describes the purification of TAB by refluxing the crude TAB with activated charcoal, aq. FeCl$_3$ solution and hydrazine hydrate (yield of TAB: 83.2% containing ≧10 ppm Cu). Three more patents (U.S. Pat. Nos. 4,433,168 and 5,235,105 and Eur. Pat. Appl. EP 522,577) describe the purification of crude TAB (obtained from ammonolysis of DCB with copper catalyst) by crystallizing it in water in presence of 0-5% by weight of activated carbon and about 1-2% by weight of a water-soluble reducing agent (alkali metal dithionate or alkali metal sulfite) at temperature of 100-140° C., under nitrogen atmosphere (yield of TAB: 88.2% of theory with only 10 ppm Cu).

In the second method for producing TAB, which has generated substantial interest, the starting material is benzidine which is acetylated with acetic anhydride, to form N,N-diacetylbenzidine. The latter compound is then nitrated with conc. HNO$_3$ to form 3,3'-dinitro-N,N-diacetylbenzidine which is base hydrolyzed to form 3,3'-dinitrobenzidine. This is then reduced by any of various means to form TAB [H. Vogel and C. S. Marvel, J. Poly. Sci. Part AI, 1531(1963)].

The third method describes the production of TAB from biphenyl which comprises the following six steps: (1) acetylating the biphenyl in the presence of an appropriate Friedel-Crafts catalyst to obtain 4,4'-diacetylbiphenyl (DAcB); (2) oximating the DAcB to form DAcB dioxime; (3) subjecting the dioxime to a double Beckmann rearrangement to obtain N,N-diacetylbenzidine. (DiAcBz); (4) Nitrating the DiAcBz to obtain 3,3'-dinitro-N,N'-diacetylbenzidine (DNAcBz); (5) removing the acetyl groups of the DNAcBz by basic hydrolysis to form 3,3'-dinitrobenzidine (DNB) and (6) reducing the nitro groups of DNB to form TAB (U.S. Pat. No. 5,041,666).

The fourth method for the preparation of TAB involves three steps comprising biaryl aryl coupling of 2-nitro-4-bromoacetamide (NBA) catalyzed by sulfilimine based palladacycles as catalysts followed by the basic hydrolysis of acetyl group and the reduction of nitro groups with conventional reducing agents (U.S. Pat. No. 6,979,749)

Although the above methods are used widely, there are various disadvantages associated with the foregoing methods.

a. The use of benzidine, for example, as one of the raw materials, is undesired since it is a known carcinogen.

b. Direct ammonolysis of DCB catalyzed by copper salts requires high temperatures (200°-300° C.) at a pressure of 900-1000 psig, which causes the manufacturing process to be hazardous. The use of such harsh reaction conditions is undesired.

c. Direct ammonolysis of DCB as disclosed by the prior art methods generates tarry materials, which always accompany the DAB produced.

d. Direct ammonolysis also causes the formation of stable complexes, where copper is likely complexed with DAB in situ, requiring the extraction of DAB from the complex. Furthermore, direct ammonolysis also causes the formation of other stable complexes, where copper is likely complexed with the corresponding triaminobiphenyl. This impurity must be removed during the manufacturing process.

e. The Suzuki type biaryl coupling of boronic acid process catalyzed by sulfilimine palladacycles is not economical as it involves costly boronic acid.

f. Lastly, the prior art methods utilize relatively expensive starting materials. Thus any method for producing DAB utilizing cheaper raw materials, which is both safer and easier to handle, would be very desirable.

OBJECTIVES OF THE INVENTION

The main objective of the present invention is to provide a novel reusable transition metal complex catalyst useful for the preparation of highly pure quality 3,3'-diaminobenzidine (DAB), and their analogues.

Another objective of the present invention is to provide a process for the preparation of highly pure quality 3,3'-diaminobenzidine (DAB), and its analogues.

Yet another objective of the present invention is to provide sulfonamide-based palladium complex and transition metals such as Cu, Ni, and Rh as an efficient catalyst for the Ullmann type biaryls coupling of substituted 4-halo-2-nitroaniline to obtain substituted 3,3'-dinitrobenzidine (DNB) which on reduction of nitro group yielded substituted DAB in high yields.

Yet another objective of the present invention is to utilize non-carcinogenic substituted 4-halo-2-nitroaniline for the coupling so as to obtain a substituted DAB.

Still another object of the present invention is to provide a process for the preparation of highly pure quality 3,3'-diaminobenzidine (DAB) with the overall yield in the range of 60 to 70%.

SUMMARY OF THE INVENTION

Accordingly the present invention provides a novel transition metal complex catalyst useful for the preparation of 3,3'-diaminobenzidine and its analogues and having a general formula:

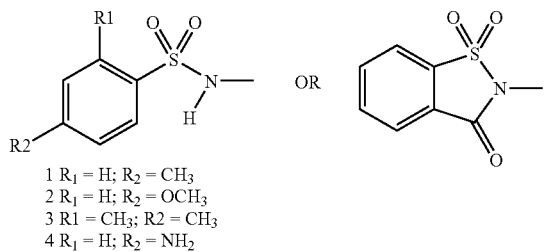

wherein X1 = X2 =

1 $R_1$ = H; $R_2$ = $CH_3$
2 $R_1$ = H; $R_2$ = $OCH_3$
3 R1 = $CH_3$; R2 = $CH_3$
4 $R_1$ = H; $R_2$ = $NH_2$

In an embodiment of the present invention the transition metal complex catalyst obtained is selected from palladium sulphonamide complex of formula 6 and bis[chloro N sacchrin palladium (II) complex of formula 8.

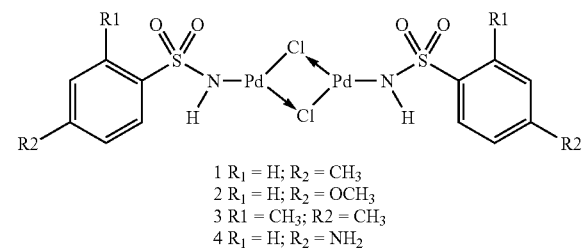

Formula 6

1 $R_1$ = H; $R_2$ = $CH_3$
2 $R_1$ = H; $R_2$ = $OCH_3$
3 R1 = $CH_3$; R2 = $CH_3$
4 $R_1$ = H; $R_2$ = $NH_2$

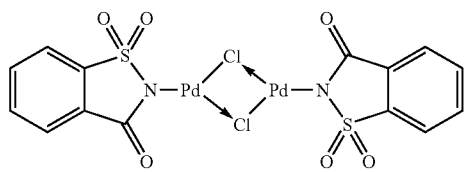

Formula 8

The present invention further provides a process for the preparation of transition metal complex catalyst, of general formula:

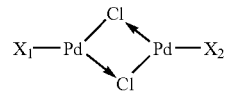

wherein X1 = X2 =

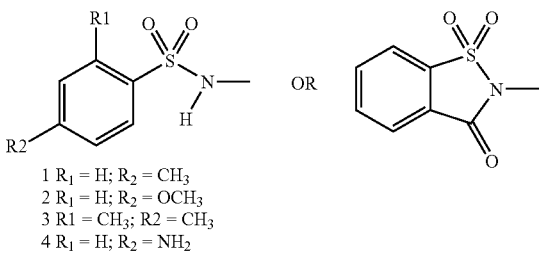

1 $R_1$ = H; $R_2$ = $CH_3$
2 $R_1$ = H; $R_2$ = $OCH_3$
3 R1 = $CH_3$; R2 = $CH_3$
4 $R_1$ = H; $R_2$ = $NH_2$ and the said process comprising the steps of:

a) reacting palladium chloride and lithium chloride in methanol under stirring for a period of 2-3 hours at a temperature of 25°-35° C., b) adding sodium acetate and methanolic solution of a compound selected from sulphonamide of formula 5 and saccharine of formula 7 to the above said resultant reaction mixture followed by stirring for a period of 70-75 hrs at a temperature of 25°-30° C.,

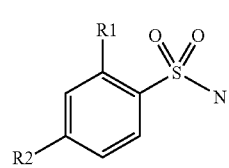

Formula 5

-continued

Formula 7 c) adding distilled water to the above said resultant reaction mixture to precipitate out the solid mass followed by filtration, washing with water and drying by known method to obtain the desired palladium complex.

In an embodiment of the present invention the palladium complex obtained is selected from palladium sulphonamide complex of formula 6 and bis[chloro N sacchrin palladium (II) complex of formula 8.

Formula 6

1 $R_1$ = H; $R_2$ = $CH_3$
2 $R_1$ = H; $R_2$ = $OCH_3$
3 $R1$ = $CH_3$; $R2$ = $CH_3$
4 $R_1$ = H; $R_2$ = $NH_2$

Formula 8

The present invention further provides a process for the preparation of 3,3'-diaminobenzidine and its analogues having general formula 1

Formula 1

R = H, $CH_3$ OR $CO_2H$ and the said process comprising the steps of:
a) haloginising substituted 2-nitroaniline of formula 4 to the corresponding 4-halo-2nitroaniline of formula 3 on treating with halide in acetic acid by known method, Formula 4:

R = H, $CH_3$ OR $CO_2H$

Formula 3:

R = H, $CH_3$ OR $CO_2H$
X = Br OR I b) homocoupling of substituted 4-halo-2-nitroaniline of formula 3 using transition metal complex catalyst preferably selected from palladium sulphonamide complex of formula 6 and bis[chloro N sacchrin palladium (II) complex of formula 8 in the presence of an organic base, at a temperature of 75°-125° C., under inert atmosphere, to obtain a corresponding substituted 3,3'-dinitrobenzidine of formula 2, Formula 6

1 $R_1$ = H; $R_2$ = $CH_3$
2 $R_1$ = H; $R_2$ = $OCH_3$
3 $R1$ = $CH_3$; $R2$ = $CH_3$
4 $R_1$ = H; $R_2$ = $NH_2$

Formula 8

Formula 2

R = H, $CH_3$, $CO_2H$ c) reducing the substituted 3,3'-dinitrobenzidine of formula 2 obtained in step (b) with $SnCl_2.HO$ and neutralizing the acid with alkali hydroxide to obtain the desire product of formula 1

In an embodiment of the present invention the halide used in step (a) is selected from the group consisting of KI, $KIO_3$ and NaCl.

In yet another embodiment of the present invention the organic base used in step (b) is selected from the group consisting of diethylamine, triethylamine and cyclohexylamine.

In yet another embodiment the alkali hydroxide used in step (c) is preferably sodium hydroxide.

In yet another embodiment the purity of substituted 3,3'-diaminobenzidine of formula 1 obtained is at least 99.65%

In still another embodiment the yield of substituted 3,3'-diaminobenzidine of formula 1 is in the range of 55-75%

The present invention provides a process for the preparation of pure high quality 3,3'-diaminobenzedene (DAB) and their analogues in high yields. More particularly, it provides a process for preparation of substituted 3,3'-diaminobenzidine (DAB) involving a three step process comprising (1) A new methodology to obtain substituted 4-halo-2-nitroaniline using very cheap raw materials where, 2-nitroaniline (100 mmol) on treatment with molecular iodine or MX (M=Na, K & X=halogens) (75-125 mmol), $MXO_n$ (M=alkali metals, X=halogens, n=3 and 4) (75-125 mmol) and NaCl (150-225 mmol) in acetic acid (100-150 ml) at room temperature for 8-15 hours gives 4-halo-2-nitroaniline. (2) Ullmann type biaryl coupling of substituted 4-halo-2-nitroaniline (10 mmol) to obtain substituted 3,3'-dinitrobenzidine (DNB) using reusable transition metal catalysts such as Pd, Cu, Ni, or Rh as efficient catalyst (0.2-1.5 mol %) and organic bases such as diethyl amine, triethyl amine, cyclohexyl amine etc (10-25 mmol) in inert atmosphere at 75-125° C. for 8-18 hours. (3) The reduction of substituted 3,3'-dinitrobenzidine (DNB) (8.0 mmol) with stannous chlorides (40-70 mmol) and concentrated hydrochloric acid (20-40 ml).

DETAILED DESCRIPTION OF THE INVENTION

The present invention provides for an improved process for the preparation of pure, high quality 3,3'-diaminobenzidine (DAB) and their analogues of formula 1

Formula-1:

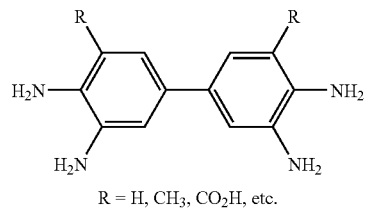

R = H, CH₃, CO₂H, etc.

which are obtained by reducing the nitro groups (using stannous chlorides as reducing agent in presence of concentrated hydrochloric acid) of substituted 3,3' dinitrobenzidine (DNB) of formula 2, Formula-2:

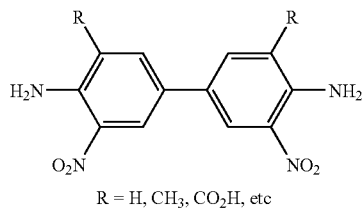

R = H, CH₃, CO₂H, etc which in turn can be obtained by the sulfonamide based palladium complexes (formulae 6 & 8) catalyzed homocoupling of substituted 4-halo-2-nitroaniline of formula 3, Formula-3:

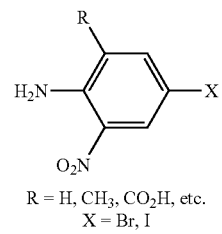

R = H, CH₃, CO₂H, etc.
X = Br, I which are easily synthesized by the halogenations of substituted o-nitroanilines of formula 4 using KI, KIO₃ or NaIO₄, NaCl in acetic acid at room temperature. (Scheme I).

Formula-4:

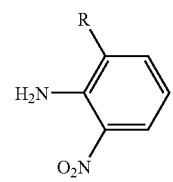

R = H, CH₃, CO₂H, etc.

In one of the feature of the present invention, the halogenation is carried out in aqueous medium.

In another feature, the addition of additive NaCl increases the reactivity and yield of the halogenated product, often reaching 100%.

The halogenation may be carried out at temperature ranging from 0-50° C., more particularly at 25° C.

Scheme 1: Preparation of TAB

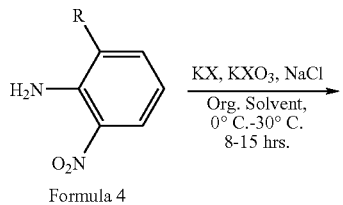

Formula 4

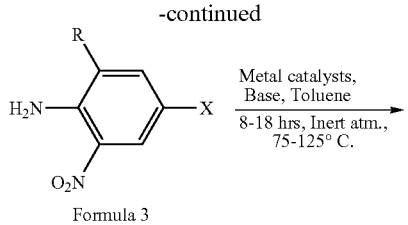

Formula 3

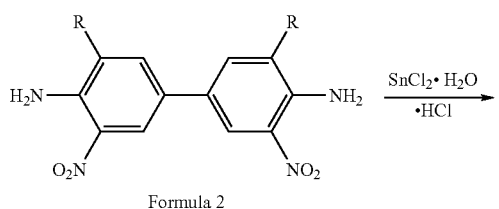

Formula 2

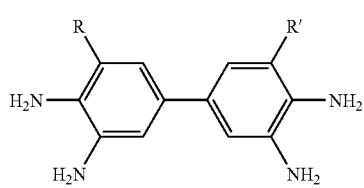

Formula 1

R = H, CH₃, CO₂H
X = Br, I

The catalyst used in the present invention is transition metals such as Pd, Cu, Ni, or Rh at 0.2-1.5 mol %.

The palladium complexes used have a general formula (6 and 8) wherein when R1=H; R2=Me or R1=H; R2=NH₂ or R=Me; R1=H or R2=OMe or R1=R2=Me are used in catalytic amounts in Ullmann type biaryl coupling with a turnover number typically in the range of 445.

The palladium complex formula (8) can be reused for the homo coupling without any appreciable loss of the catalytic activity.

The solvent used may be selected from a range of organic solvents, such as, but are not limited to, acetonitrile, acetone, toluene, methanol, acetic acid and water.

Chemistry:

The first step of the process involves regioselective mono halogenation of 2-nitroaniline, which proceeds through in situ formation of iodine monochloride (ICl) as the active iodinating species. The monohalogenation of aromatic compounds using KIO₃/KX/NaCl is milder and is inactive against easily oxidizable groups like aldehyde. This reaction does not need highly inert condition and was carried out at room temperature with high yield and purity. It was found that the addition of NaCl increases the reactivity and yield. Oxidants which are known to oxidize metal halides to liberate halogens, for example, mCPBA, Oxone, KIO₃, etc. iodine source (nBu₄NI, I₂ and NaI) and additives (LiBr, NaF, NCS) have been screened and found that KIO₃/KX/NaCl combination has the maximum reactivity (Table-1). The iodination of 2-nitroaniline was successfully scaled-up to afford multigram quantities of 4-iodo 2-nitroaniline and this condition was found to be mild and not extremely exothermic. The mono iodination was achieved using the present protocol in 98% isolated yield.

The homocoupling of 4-iodo-2-nitroaniline is catalyzed by a new water soluble and reusable palladium complex (formula 8) with saccharin backbone. Similar types of sulfonamide palladium complex have been prepared from using substituted sulfonamide (formula 6) and PdCl₂ in MeOH (Scheme 2). The homocoupling requires minimum quantity of catalyst loading and gave excellent yield of homocoupled product (Formula 2). 3,3' Dinitrobenzidine (DNB) is insoluble in toluene and separates out of the reaction mixture after the reaction. After the simple filtration, the palladium complex present in the toluene is once again used for the homo coupling of 4-iodo-2-nitroaniline and it was found that the catalyst was extremely active for the coupling reaction. Table 2 shows the results obtained from screening experiments using several Palladium catalysts for the homocoupling of 4-iodo-2-nitroaniline.

The reduction of the nitro group is carried out using NaOH/SnCl₂/con. HCl strictly following the reported procedure. After the reduction the crude TAB is recrystallized from water and its pure form is colorless and sharply melts at 179. 9° C. pure (from DSC). Thus obtained TAB had high purity of 99.65% (determined from HPLC, FIG. 1).

The process of the present invention is described herein with reference to examples, which are illustrative only and should not be construed to limit the scope of the present invention in any manner.

Scheme 2: Preparation of Palladium Sulfonamide and Saccharin complexes

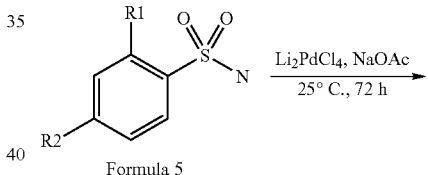

Formula 5

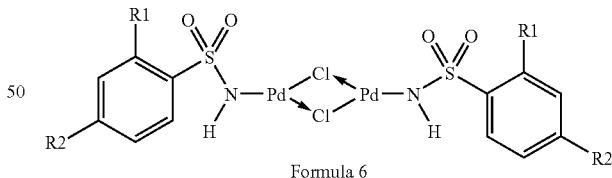

Formula 6

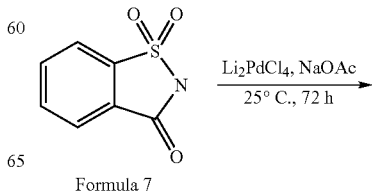

Formula 7

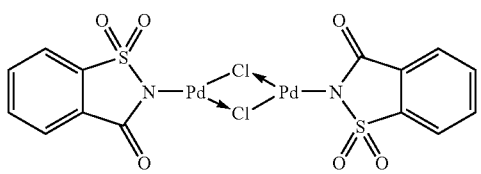

Formula 8

1 $R_1$ = H; $R_2$ = $CH_3$
2 $R_1$ = H; $R_2$ = $OCH_3$
3 $R_1$ = $CH_3$; $R_2$ = $CH_3$
4 $R_1$ = H; $R_2$ = $NH_2$

HPLC of TAB was conducted under following conditions:

| Column: | Lichrospher RP-8 25 cm |
| --- | --- |
| Mobile Phase: | MEOH:BUFFER (pH-3) 10:90 |
| Wavelength: | 254 nm |
| Flow rate: | 0.7 ml/min |

The Report obtained was:

Detector A (254 nm)

| Peak No. | Retention Time | Area | Area Percent |
| --- | --- | --- | --- |
| 1 | 3.805 | 2973 | 0.07 |
| 2 | 4.762 | 4076350 | 99.65 |
| 3 | 11.083 | 9093 | 0.22 |
| 4 | 14.645 | 2360 | 0.06 |
| Totals | | 4090776 | 100.00 |

TABLE 1

Iodination of 2-nitroaniline

| No. | Oxidant[a] | iodine source | additive | Yield[b] (%) |
| --- | --- | --- | --- | --- |
| 1 | $NaIO_4$ | KI | — | 55 |
| 2 | $KIO_3$ | KI | NaCl | 98 |
| 3 | $NaIO_4$ | KI | NaCl | 98 |
| 3 | Oxone | KI | NaCl | 47 |
| 5 | $KBrO_3$ | KI | NaCl | 71 |
| 6 | mCPBA | KI | NaCl | 56 |
| 7 | $V_2O_5$ | KI | NaCl | 32[c] |
| 8 | $HIO_4$ | KI | NaCl | 87 |
| 9 | $NaIO_4$ | NaI | NaCl | 84 |
| 10 | $NaIO_4$ | $NBu_4^+I^-$ | NaCl | 82 |
| 11 | $NaIO_4$ | $I_2$ | NaCl | 95[d] |
| 12 | $NaIO_4$ | KI | NaF | 58 |
| 13 | $NaIO_4$ | KI | LiBr | 100[f] (16:84)[e] |
| 14 | $NaIO_4$ | KI | NCS | 73 |

Thus, the obtained TAB had high purity of 99.65 percent.
[a]Stoichiometry (molar equivalent): oxidant:iodine source:additive = 1:1:2 unless otherwise stated
[b]Isolated yield by column chromatographic purification
[c]Reaction was done at 60° C.; Yield at room temperature was <5%
[d]0.5 equivalent of molecular iodine was used
[e]Iodo and bromo products formed in the ratio 16:84 respectively
[f]Conversion was found by GC-MS

TABLE 2

Screening of palladium catalyst for Ullmann coupling of 4-iodo-2-nitroaniline

| No. | Pd catalyst | base[a] | solvent[b] | Yield of 3,3'-dinitrobenzidine (%)[c] (coupled product) | Yield of 4-iodo-o-phenylenediamine (%)[c] (Reduced product) |
| --- | --- | --- | --- | --- | --- |
| 1 | $PdCl_2$ | TEA | DMF/NMP | — | — |
| 2 | $PdCl_2$ | DIEA | DMF/NMP | — | 45 |
| 3 | $Pd(OAc)_2$ | DIEA | toluene | 8 | 44 |
| 4 | $Pd(OAc)_2$ | TEA | DMF/NMP | 12 | 41 |
| 5 | $Pd(PPh_3)_4$ | DIEA | DMF/NMP | 16 | 46 |
| 6 | $Pd(PPh_3)_4$ | TEA | DMF/NMP | — | — |
| 7 | Pd saccharin complex | TEA | DMF/NMP | — | — |
| 8 | Pd saccharin complex | TEA | toluene | 89 | — |

[a]TEA = Triethyl amine; DIEA = Diisopropyl ethylamine
[b]NMP = N-methl pyrrolidine; DMF = N,N-Dimethyl formamide
[c]Yield determined from GC-MS The following examples are given by the way of illustration and therefore should not be construed to limit the scope of the invention.

EXAMPLE 1

Preparation of Palladium Complex Formula 6 where in R1=H and R2=CH$_3$

Two-necked 25 ml RB flask was charged with PdCl$_2$ (0.177 g, 1 mmol), LiCl (0.100 g, 2.4 m mol) and MeOH (2 ml). The resulting reaction mixture was stirred under argon atmosphere at 25° C. for 2.5 h. Then to the same reaction was added NaOAc (0.123 g, 1.5 mmol), and a solution of the corresponding sulfonamide (formula 5) (0.171 g, 1 mmol) in MeOH (2 ml). The resulting reaction mixture was stirred at 25° C. for 72 h. Then distilled water (6 ml) was added to it and the solid was filtered on sintered funnel, washed with water and dried under reduced pressure (5 mm) for 3 h to afford palladium complex (formula 6) where in R=H and R1=H as brown colored solid. Yield: 63%, mp: 195° C. (charred)

EXAMPLE 2

Preparation of Palladium Complex Formula 6 where in R1=H and R2=NH$_2$

Two-necked 25 ml RB flask was charged with PdCl$_2$ (0.177 g, 1 mmol), LiCl (0.100 g, 2.4 m mol) and MeOH (2 ml). The resulting reaction mixture was stirred under argon atmosphere at 25° C. for 2.5 h. Then to the same reaction was added NaOAc (0.172 g, 1.5 mmol), and a solution of the corresponding sulfonamide formula 5 (0.293 g, 1 mmol) in MeOH (2 ml). The resulting reaction mixture was stirred at 25° C. for 72 h. Then distilled water (6 ml) was added to it and the solid was filtered on sintered funnel, washed with water and dried under reduced pressure (5 mm) for 3 h to afford palladium complex (formula 6) where in R=H and R1=Me as brown colored solid. Yield: 66%, mp: 305° C. (charred)

EXAMPLE 3

Preparation of Palladium Complex Formula 6 where in R1=H and R2=OCH$_3$

Two-necked 25 ml RB flask was charged with PdCl$_2$ (0.177 g, 1 mmol), LiCl (0.100 g, 2.4 m mol) and MeOH (2 ml). The resulting reaction mixture was stirred under argon atmosphere at 25° C. for 2.5 h. Then to the same reaction was added NaOAc (0.123 g, 1.5 mmol), and a solution of the corresponding sulfonamide (formula 5) (0.187 g, 1 mmol) in MeOH (2 ml). The resulting reaction mixture was stirred at 25° C. for 72 h. Then distilled water (6 ml) was added to it and the solid was filtered on sintered funnel, washed with water and dried under reduced pressure (5 mm) for 3 h to afford palladium complex (formula 6) where in R=H and R1=Me as brown colored solid. Yield: 68%, mp: 198° C. (charred.)

EXAMPLE 4

Preparation of Palladium Complex Formula 6 where in R1=CH$_3$ and R2=CH$_3$

Two-necked 25 ml RB flask was charged with PdCl$_2$ (0.177 g, 1 mmol), LiCl (0.100 g, 2.4 m mol) and MeOH (2 ml). The resulting reaction mixture was stirred under argon atmosphere at 25° C. for 2.5 h. Then to the same reaction was added NaOAc (0.123 g, 1.5 mmol), and a solution of the corresponding sulfonamide (formula 5) (0.185 g, 1 mmol) in MeOH (2 ml). The resulting reaction mixture was stirred at 25° C. for 72 h. Then distilled water (6 ml) was added to it and the solid was filtered on sintered funnel, washed with water and dried under reduced pressure (5 mm) for 3 h to afford palladium complex (formula 6) where in R=H and R1=Me as brown colored solid. Yield: 72%, mp: 160° C. (charred.)

EXAMPLE 5

Preparation of Saccharin Palladium Complex Formula 8

Two-necked 25 ml RB flask was charged with PdCl$_2$ (0.177 g, 1 mmol), LiCl (0.100 g, 2.4 m mol) and MeOH (2 ml). The resulting reaction mixture was stirred under argon atmosphere at 25° C. for 2.5 h. Then to the same reaction was added NaOAc (0.123 g, 1.5 mmol), and a solution of saccharin (formula 7) (0.183 g, 1 mmol) in MeOH (2 ml). The resulting reaction mixture was stirred at 25° C. for 72 h. Then distilled water (6 ml) was added to it and the solid was filtered on sintered funnel, washed with water and dried under reduced pressure (5 mm) for 3 h to afford palladium complex (formula 8) where in R=H and R1=Me as brown colored solid. Yield: 75%, mp: 240° C. (decomp.)

EXAMPLE 6

Preparation of 4-iodo-2-nitroaniline Formula 3 where in R=H

In a round bottom flask, a mixture of o-nitro aniline (formula 4) (13.7 g, 100 mmol), and potassium iodide (16.6 g, 100 mmol), potassium periodate (21.4 g, 100 mmol), sodium chloride (11.7 g, 200 mmol) in acetic acid and water (9:1) was stirred for 8-15 hours at room temperature. The reaction mixture was then poured over chopped ice and extracted with dichloromethane. The extract was further washed twice with water, then brine solution and dried over anhydrous sodium sulfate. On removal of dichloromethane 4-iodo-2-nitro aniline (formula 3) was obtained in 100% yield (26.4 g). The product was analyzed by the analytical methods like $^1$H & $^{13}$C NMR and GC-MS for its purity.

EXAMPLE 7

Preparation of Substituted 4-iodo-2-nitroaniline Formula 3 where in R=CH$_3$

In a round bottom flask, a mixture of o-nitro aniline formula 4 where in R=Me (2.96 g, 20 mmol), and potassium iodide (3.32 g, 20 mmol), potassium periodate (4.28 g, 100 mmol), sodium chloride (2.3 g, 40 mmol) in acetic acid and water (9:1) was stirred for 8 hours at room temperature. The reaction mixture was then poured over chopped ice and extracted with dichloromethane. The extract was further washed twice with water, then brine solution and dried over anhydrous sodium sulfate. On removal of dichloromethane 4-iodo-2-nitro aniline was obtained in 95% yield (5.2 g). The product was analyzed by the analytical methods like $^1$H & $^{13}$C NMR and GC-MS for its purity.

EXAMPLE 8

Preparation of Substituted 4-iodo-2-nitroaniline Formula 3 where in R=CO$_2$H (Acid)

In a round bottom flask, a mixture of o-nitro aniline formula 4 where in R=CO$_2$H (3.64 g, 20 mmol), and potassium iodide (3.32 g, 20 mmol), potassium periodate (4.28 g, 20 mmol), sodium chloride (2.3 g, 40 mmol) in acetic acid and water (9:1) was stirred for 8-15 hours at room temperature. The reaction mixture was then poured over chopped ice and extracted with dichloromethane. The extract was further washed twice with water, then brine solution and dried over anhydrous sodium sulfate. On removal of dichloromethane 4-iodo-2-nitro aniline was obtained in 92% yield (5.67 g). The product was analyzed by the analytical methods like $^1$H & $^{13}$C NMR and GC-MS for its purity.

Homocoupling of Substituted Nitro Aniline

EXAMPLE 9

Preparation of 3,3'-dinitrobenzidine (DNB) of Formula 2 where in R═H

In a single neck round bottomed flask equipped with condenser, nitrogen balloon and stirring magnetic bar were placed 4-iodo-2-nitroaniline (2.54 g, 10 mmol), of formula 3 where in R═H, triethylamine (2.02 g, 20 mmol) and palladium complex (0.0325 g, 0.5 mol %) in anhydrous toulene (35 ml). The whole reaction set up was flushed with nitrogen and stirred for 12 hours at 90-130° C. The coupled product 3,3'-dinitrobenzidine (DNB) obtained was reddish in color insoluble in toluene and separated out from the solvent. Decantation and washing with petroleum ether gave 3,3'-dinitrobenzidine (DNB) in 79% yield (2.0 g). The melting point of the product was 280° C.

EXAMPLE 10

Preparation of Substituted 3,3'-dinitrobenzidine (DNB) of Formula 2 where in R═CH$_3$ In a single neck round bottomed flask equipped with condenser, nitrogen balloon and stirring magnetic bar were placed substituted 4-iodo-2-nitroaniline of formula 3 where in R═CH$_3$ (4.932 g, 18 mmol), triethylamine (36.36 g, 36 mmol) and palladium complex (0.0585 g, 0.5 mol %) in anhydrous toulene (50 ml). The whole reaction set up was flushed with nitrogen and stirred for 8 hours at 90-130° C. The coupled product 3,3'-dinitrobenzidine (DNB) obtained was reddish in color insoluble in toluene and separated out from the solvent. Decantation and washing with petroleum ether gave 3,3'-dinitrobenzidine (DNB) in 67% yield (1.35 g). The melting point of the product was 280° C.

EXAMPLE 11

Preparation of Substituted 3,3'-dinitrobenzidine (DNB) of Formula 2 where in R═CO$_2$H In a single neck round bottomed flask equipped with condenser, nitrogen balloon and stirring magnetic bar were placed substituted 4-iodo-2-nitroaniline of formula 3 where in R═CO$_2$H (5.54 g, 18 mmol), triethylamine (36.36 g, 36 mmol) and palladium complex (0.0585 g, 0.5 mol %) in anhydrous toulene (50 ml). The whole reaction set up was flushed with nitrogen and stirred for 8 hours at 90-130° C. The coupled product 3,3'-dinitrobenzidine (DNB) obtained was reddish in color insoluble in toluene and separated out from the solvent. Decantation and washing with petroleum ether gave 3,3'-dinitrobenzidine (DNB) in 75% yield (2.43 g). The melting point of the product was 280° C.

Reduction of Nitro Group

EXAMPLE 12

Preparation of 3,3'-diaminobenzidine (DAB) of Formula 1 where in R═H

A 50 ml single neck round bottomed flask equipped with condenser, and stirring magnetic bar were placed SnCl$_2$.2H$_2$O (12 g, 53 mmol) and 25 ml concentrated hydrochloric acid and reaction mixture was stirred and than 3,3'-dinitrobenzidine (DNB) of formula 2 where in R═H (2.16 g, 7.9 mmol) was added in small portions over 15 minute to maintain the reaction temperature less than 60° C. The thick slurry was then stirred for additional 2 hours at 40° C. to complete the reduction. The salt of the tetramine was precipitated out, which was neutralized with cold 10% NaOH solution and the solid filtered out, washed with water dried under vacuum to give 3,3'-diaminobenzidine (DAB) in 74% yield (1.26 g).

EXAMPLE 13

Preparation of Substituted 3,3'-diaminobenzidine (DAB) of Formula 1 where in R═CH$_3$ A 50 ml single neck round bottomed flask equipped with condenser, and stirring magnetic bar were placed SnCl$_2$.2H$_2$O (6 g, 26.5 mmol) and 12.5 ml concentrated hydrochloric acid and reaction mixture was stirred and than 3,3'-dinitrobenzidine formula 2 where in R═CH3 (DNB) (1.176 g, 4 mmol) was added in small portions over 15 minute to maintain the reaction temperature less than 60° C. The thick slurry was then stirred for additional 2 hours at 40° C. to complete the reduction. The salt of the tetramine was precipitated out, which was neutralized with cold 10% NaOH solution and the solid filtered out, washed with water dried under vacuum to give 3,3'-diaminobenzidine (DAB) in 70% yield (0.655 g).

EXAMPLE 14

Preparation of Substituted 3,3'-diaminobenzidine (DAB) of Formula 1 where in R═CO$_2$H A 50 ml single neck round bottomed flask equipped with condenser, and stirring magnetic bar were placed SnCl$_2$.2H$_2$O (6 g, 26.5 mmol) and 15 ml concentrated hydrochloric acid and reaction mixture was stirred and than 3,3'-dinitrobenzidine (DNB) formula 2 where in R═CO$_2$H (1.8 g, 5 mmol) was added in small portions over 15 minute to maintain the reaction temperature less than 60° C. The thick slurry was then stirred for additional 2 hours at 40° C. to complete the reduction. The salt of the tetramine was precipitated out, which was neutralized with cold 10% NaOH solution and the solid filtered out, washed with water dried under vacuum to give 3,3'-diaminobenzidine (DAB) in 69% yield (1.035 g).

The Advantages of the Present Invention are:
1. In all the three steps of the reactions, the isolation of the product can be performed either by extraction or by simple filtration. None of the steps required the classical purification technique like column chromatography.
2. A new and versatile method for the regioselective mono iodination of substituted 2-nitro anilines has been developed and employed.

3. The use of novel catalysts (palladacycle) in this process makes it possible to carry out the reactions under milder and safer conditions.
4. The transition metal catalyst used for the homocoupling of 4-halo-2-nitroaniline can be easily separated out and recycled without loss of activity. The turn over number of the catalyst is moderate (i.e. 445).
5. The turnover number of biaryl formation (Ullmann type coupling) is generally in the range of 445 and the conversion and the selectivity are excellent. The reduced product is diminished to great extent.
6. The product DAB can be produced without any metal or their salt contamination thus enhancing the purity of DAB. The purity of DAB was found to be 99.65% without crystallization.
7. No other side-product was found. Total destruction of the product at elevated temperature also was diminished.
8. Quantitative conversions are obtained in all the three steps, i.e. halogenation, homocoupling and reduction of nitro to amine group. The overall yield of the all the three steps is 63.6%.
9. All the reagents used here are easily accessible, easy to handle, environmentally safe, and excellent yield has been achieved.

The invention claimed is:

1. A process for the preparation of 3,3'-diaminobenzidine and its analogues having general formula 1

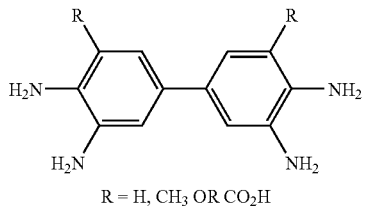

Formula 1

R = H, CH$_3$ OR CO$_2$H and the said process comprising the steps of:
a) haloginising substituted 2-nitroaniline of formula 4 to the corresponding 4-halo-2nitroaniline of formula 3 on treating with halide in acetic acid by known method, Formula 4:

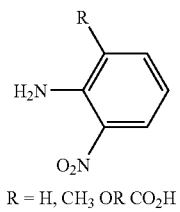

R = H, CH$_3$ OR CO$_2$H

Formula 3:

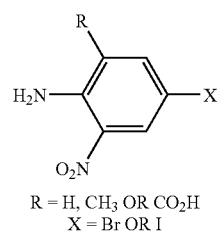

R = H, CH$_3$ OR CO$_2$H
X = Br OR I b) homocoupling of substituted 4-halo-2-nitroaniline of formula 3 using transition metal complex catalyst preferably selected from palladium sulphonamide complex of formula 6 and bis[chloro N saccharin palladium (II) complex of formula 8 in the presence of an organic base, at a temperature of 75°-125° C., under inert atmosphere, to obtain a corresponding substituted 3,3'-dinitrobenzidine of formula 2,

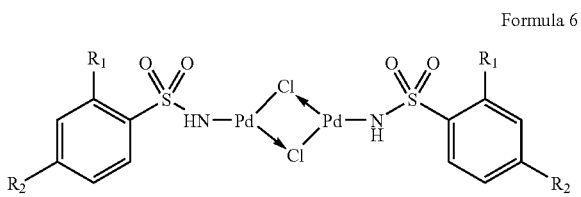

Formula 6 wherein R$_1$ is hydrogen and R$_2$ is methyl, methoxy or amino or R$_1$ and R$_2$ are both methyl

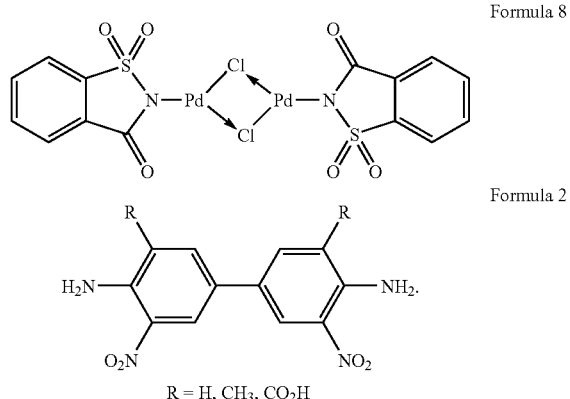

Formula 8

Formula 2

R = H, CH$_3$, CO$_2$H c) reducing the substituted 3,3'-dinitrobenzidine of formula 2 obtained in step (b) with SnCl$_2$.HO and neutralizing the acid with alkali hydroxide to obtain the product of formula 1.

2. A process according to claim 1, wherein the halide used in step (a) is selected from the group consisting of KI, KIO$_3$ and NaCl.

3. A process according to claim 1, wherein the catalyst palladium sulphonamide complex of formula 6 or bis[chloro N sacchrin palladium (II) complex of formula 8 used is reusable.

4. A process according to claim 1, wherein the organic base used in step (b) is selected from the group consisting of diethylamine, triethylamine and cyclohexylamine.

5. A process according to claim 1, wherein the alkali hydroxide used in step (c) is preferably sodium hydroxide.

6. A process according to claim 1, wherein the purity of substituted 3,3'-diaminobenzidine of formula 1 obtained is at least 99.65%.

7. A process according to claim 1, wherein the yield of substituted 3,3'-diaminobenzidine of formula 1 is in the range of 55-75%.

* * * * *